United States Patent [19]
McKean et al.

[11] Patent Number: 5,908,427
[45] Date of Patent: *Jun. 1, 1999

[54] SURGICAL STAPLING APPARATUS AND METHOD

[75] Inventors: Wanda L. McKean, Stamford; Matthew Hain, New Haven; Ilya S. Koyfman, Orange, all of Conn.

[73] Assignee: United States Surgical Corporation, Norwalk, Conn.

[*] Notice: This patent is subject to a terminal disclaimer.

[21] Appl. No.: 08/866,506

[22] Filed: May 30, 1997

Related U.S. Application Data

[60] Continuation of application No. 08/664,658, Jun. 17, 1996, which is a division of application No. 08/132,601, Oct. 6, 1993, Pat. No. 5,542,594.

[51] Int. Cl.$^6$ .................................................. A61B 17/00
[52] U.S. Cl. .............................................................. 606/139
[58] Field of Search ..................... 606/139, 144, 606/148

[56] References Cited

U.S. PATENT DOCUMENTS

| 2,671,444 | 3/1954 | Pease, Jr. . |
| 3,054,406 | 9/1962 | Usher . |
| 3,079,606 | 3/1963 | Bobrov et al. . |

(List continued on next page.)

FOREIGN PATENT DOCUMENTS

| 0334046 | 2/1989 | European Pat. Off. . |
| 0325195 | 7/1989 | European Pat. Off. . |

OTHER PUBLICATIONS

"Wedge Resection of Lung Without Staples on Specimen," Arthur C. Beall, Jr., M.D., Javier A. Lafuente, M.D., and James W. Jones, M.D., Ph.D., Ann. Thorac. Surg, 1995; 59; 1038–46, pp. 1041–1043, Copyright 1995 by The Society of Thoracic Surgeons.

"How Prolonged is 'Prolonged Air Leak'?"; Samuel A. Adebonojo, M.D., Ann. Thorac. Surg.; 1995; 59; 544–51, p. 549, Copyright 1995 by The Society of Thoracic Surgeons.

"Cystic and Bullous Lung Disease"; M.E. Ribet, M.D.; Ann Thorac. Surg. 1992; 53:1147–52; pp. 1147–1150, Copyright 1992 by The Society of Thoracic Surgeons.

"Peri–Strips™ Staple Line Reinforcement—Sleeve Configuration," Care and Handling Instructions, by Bio–Vascular, Inc., Saint Paul, MN, Aug. 1994.

"Peri–Strips® Staple Line Reinforcement Sleeve Configuration", Hospital Price Schedule, by BioVascular, Inc., Saint Paul, MN, Nov. 1, 1994.

"Long Term Results of Surgery For Bullous Emphysema," Muiris X. Fitzgerald, M.D., Patrick J. Keelan, M.D., David W. Cugell, M.D., Edward A. Gaensler, M.D., The Journal of Thoracic and Cardiovascular Surgery, vol. 68, No. 4, Oct., 1974, pp. 566–587.

"Anesthesia for Thoracoscopic Laser Ablation of Bullous Emphysema"; Steven J. Barker, Ph.D., M.D., Chris Clarke, MB, Narendra Trivedi, M.D., John Hyatt, BS, Meg Fynes, BS. Peter Roessler, BS, Anesthigiology, V 78, No. 1, Jan. 1993, pp. 44–50.

(List continued on next page.)

*Primary Examiner*—Michael Buiz
*Assistant Examiner*—Vikki Trinh

[57] ABSTRACT

A surgical stapling apparatus having tissue bolstering material releasably attached thereto for application of the material and staples to body tissue is disclosed. The tissue bolstering material is preferably releasably held to surfaces of the stapling apparatus through pins, clips or similar securing structures. The tissue bolstering material can be either planar or tubular in configuration. Preferably, both the anvil portion and the fastener ejecting portion of the stapler are at least partially covered with the tissue bolstering material. In use, tissue is disposed between the anvil portion and the stapling portion of the instrument and the instrument is fired. The tissue bolstering material is thereby secured to the tissue and releasably detaches from the stapler upon withdrawal of the stapler from the surgical site.

15 Claims, 9 Drawing Sheets

U.S. PATENT DOCUMENTS

| | | |
|---|---|---|
| 3,108,357 | 10/1963 | Liebig . |
| 3,122,140 | 2/1964 | Crowe, Jr. . |
| 3,124,136 | 3/1964 | Usher . |
| 3,272,204 | 9/1966 | Artandi et al. . |
| 3,276,448 | 10/1966 | Kronenthal . |
| 3,284,557 | 11/1966 | Polansky . |
| 3,463,158 | 8/1969 | Schmitt et al. . |
| 3,490,675 | 1/1970 | Green et al. . |
| 3,620,218 | 11/1971 | Schmitt et al. . |
| 3,636,956 | 1/1972 | Schneider . |
| 3,688,317 | 9/1972 | Kurtz . |
| 3,739,773 | 6/1973 | Schmitt et al. . |
| 3,875,937 | 4/1975 | Schmitt et al. . |
| 3,937,223 | 2/1976 | Roth . |
| 3,953,566 | 4/1976 | Gore .................................... 764/210 R |
| 3,962,153 | 6/1976 | Gore .................................... 260/2.5 E |
| 4,096,227 | 6/1978 | Gore ....................................... 264/210 |
| 4,128,612 | 12/1978 | Roth . |
| 4,132,839 | 1/1979 | Marans et al. . |
| 4,164,046 | 8/1979 | Cooley . |
| 4,186,448 | 2/1980 | Brekke . |
| 4,187,390 | 2/1980 | Gore .................................. 174/102 P |
| 4,215,686 | 8/1980 | Gregory et al. . |
| 4,347,847 | 9/1982 | Usher . |
| 4,354,628 | 10/1982 | Green . |
| 4,397,311 | 8/1983 | Kanshin et al. . |
| 4,452,245 | 6/1984 | Usher . |
| 4,520,817 | 6/1985 | Green . |
| 4,520,821 | 6/1985 | Schmitt et al. . |
| 4,548,202 | 10/1985 | Duncan . |
| 4,626,253 | 12/1986 | Broadmax, Jr. . |
| 4,633,861 | 1/1987 | Chow et al. . |
| 4,633,873 | 1/1987 | Dumican et al. . |
| 4,633,874 | 1/1987 | Chow et al. . |
| 4,652,264 | 3/1987 | Dumican . |
| 4,655,221 | 4/1987 | Devereux . |
| 4,702,917 | 10/1987 | Schindler . |
| 4,784,137 | 11/1988 | Kulik et al. . |
| 4,832,686 | 5/1989 | Anderson . |
| 4,838,884 | 6/1989 | Dumican et al. . |
| 4,840,626 | 6/1989 | Linsky et al. . |
| 4,865,031 | 9/1989 | O'Keefe . |
| 4,892,244 | 1/1990 | Fox et al. . |
| 4,905,692 | 3/1990 | More . |
| 4,930,674 | 6/1990 | Barak . |
| 4,955,959 | 9/1990 | Tompkins et al. . |
| 4,960,861 | 10/1990 | Bendix et al. . |
| 4,983,745 | 1/1991 | Muller et al. . |
| 5,002,551 | 3/1991 | Linksy et al. . |
| 5,011,493 | 4/1991 | Relykh et al. . |
| 5,014,899 | 5/1991 | Presty et al. . |
| 5,040,715 | 8/1991 | Green et al. . |
| 5,042,707 | 8/1991 | Taberi . |
| 5,061,281 | 10/1991 | Mares et al. . |
| 5,066,772 | 11/1991 | Tang et al. . |
| 5,079,075 | 1/1992 | Yamasaki et al. . |
| 5,102,983 | 4/1992 | Kennedy . |
| 5,156,797 | 10/1992 | Yamasaki et al. . |
| 5,176,692 | 1/1993 | Wilk et al. . |
| 5,203,864 | 4/1993 | Philips . |
| 5,263,629 | 11/1993 | Trumhull et al. . |
| 5,346,115 | 9/1994 | Perouse et al. . |
| 5,397,324 | 3/1995 | Carroll et al. . |
| 5,433,721 | 7/1995 | Hooven et al. . |
| 5,441,193 | 8/1995 | Gravener . |
| 5,503,638 | 4/1996 | Cooper et al. . |
| 5,542,594 | 8/1996 | McKean et al. . |
| 5,702,409 | 12/1997 | Rayburn et al. ........................ 606/151 |

OTHER PUBLICATIONS

"Surgical Management of Emphysema", Edward Gaensler, M.D., David Cugell, MD., Ronald Knudson, MD. and Muiris X. Fitzgerald, M.D., FRCP, FRCPI, Clinics in Chest Medicine, vol. 4, No.3, Sep. 1983, pp. 443–463.

"Thoracoscopic Laser Ablation of Pulmonary Bullae"; Matthew Brenner, MD, Raouf A. Kayaleh, M.D., Eric N. Milne, M.D., Luise Della Bella, RN., Kathryn Osann, PhD, Yona Tadir, MD, Michael W. Berns, PhD, and Archie F. Wilson, M.D., PhD., Irvine, CA, The Journal of Thoracic and Cardiovascular Surgery, vol. 107, No. 3, Mar. 1994, pp. 883–890.

"Reinforced Staple Line in Severely Emphysematous Lungs", F.M. Juettner, M.D., P. Kohek, M.D., H. Pinter, M.D., G. Klepp, MD., and G. Friehs, M.D., Graz, Austria, J. Thorac. Cardiovasc. Surg. 1989; 97:362–3, vol. 97, No. 3, Mar. 1989, pp. 362–363.

"Optimizing Selection of Patients For Major Lung Resection"; Mark K. Gerguson, MD; Laurie B. Reeder, M.D., and Rosemarie Mick, MS, Chicago, IL, The Journal of Thoracic and Cardiovascular Surgery, vol. 109, No.2, Feb. 1995, pp. 275–283.

"Median Sternotomy for Bilateral Resection of Emphysematous Bullae"; Oriane Lima, M.D., Luis Ramos, M.D., Paulo Di Biasi, M.D., Luis Judice, M.D., and Joel D. Cooper, M.D., The Journal of Thoracic and Cardiovascular Surgery, vol. 82, No. 6, Dec. 1981, pp. 892–897.

"The Current Status of Surgery for Bullous Emphysema"; John Connolly, MD. and Archie Willson, MD the Journal of Thoracic and Cardiovascular Surgery, vol. 97, No. 3, Mar. 1989, pp. 351–361.

"Bilateral Pneumectomy (Volume Reduction) for Chronic Obstructive Pulmonary Disease", J.D. Cooper, M.D., E.P. Trulock, MD., A.N. Triantafillou, M.D., G.A. Patterson, M.D., MS. Pohl, R.N., P.A. Deloney, R.N., R.S. Sundaresan, M.D. and C.L. Roper, The Journal of Thoracic and Cardiovascular Surgery, vol. 109, No. 1, Jan. 1995, pp. 106–119.

"Lung Resections Conornitant to Coronary Artery Bypass Grafting", A. Terzi, G. Furlan, G. Magnanelli, F. Conti, P. Chiavacci, G. Petrilli, N. Ivic, European Journal of Cardio–thoracic Surgery, 1994 8:580–584.

"Surgical Treatment of Diffuse Emphysema, A, Randomized, Prospective Trial of Laser Bullectomy Versus Lung Reduction with Staples and Bovine Pericardium"; Robert McKenna, Jr. M.D., Matthew Brenner, M.D., Michael J. Mullin, M.D., Narindar Singh, M.D., and Michael Berns, Ph.D., AATS Boston, 1995, p. 176.

"Unilateral Thoracoscopic Surgical Approah For Diffuse Bullous Emphysema"; Robert J. Keenan, M.D., Rodney J. Landreneau, M.D., Frank C. Sciurba, M.D., Peter F. Ferson, M.D., Lynda S. Fetterman, M.D., Claudia M. Bowers, BSN, and Bartley P. Griffith, M.D. AATS Boston, 1995 p. 174.

"Lung Reduction as Bridge to Lung Transplantation in Pulmonary Emphysema"; Marco Zenati, M.D., Robert J. Keenan, M.D., Rodney J. Landreneau, M.D., Irvin L. Paradis, M.D., Peter F. Ferson, M.D. and Bartley P. Griffith, M.D., Ann. Thorac. Surg., 1995; 59; 1581–3.

Advertising Brochure: "Peri–Strips® Staple Line Reinforcement Sleeve. Configuration," May 1995, of Bio–Vascular, Inc.

Malm et al., Prevention of Postoperative Pericardial Adhesions by Closure of the Pericardium with Absorbable Polymer Patches, The Journal of Thoracic and Cardiovascular Surgery, vol. 104, No. 3, pp. 600–607, Sep. 1992.

Juettner et al., Reinforced Staple Line in Severely Emphysematous Lungs, 1989, Journal of Thoracic Cardiovascular Surgery, pp. 362–363.

Nakamura, et al., Clinical Study of Bioabsorbable PGA Sheets for Suture Reinforcement and Use as Artificial Pleura, Japan Lung Surgery Journal 40: 10, 8(1826) 1992.

Nakamura, et al., New Bioabsorbable Pledgets and Non-Woven Fabrics Made from Polyglycolide (PGA) for Pulmonary Surgery: Clinical Experience, Thoracic Cardiovascular Surg. 38 (1990) 81–85.

Cooper, Technique to Reduce Air Leaks After Resection of Emphysematous Lung, The Society of Thoracic Surgeons 1994.

Hood, Stapling Techniques Involving Lung Parenchyma, Surgical Clinics of North America, vol. 61, No. 3, Jun. 1984.

SURGICAL STAPLING APPARATUS AND METHOD

This is a continuation of U.S. application Ser. No. 08/664,658, filed Jun. 17, 1996 which is a divisional of application Ser. No. 08/132,601 filed on Oct. 6, 1993, now U.S. Pat. No. 5,542,594 issued on Aug. 6, 1996.

BACKGROUND OF THE INVENTION

1. Field of the Invention

This invention relates to apparatus for applying biocompatible surgical fabric to body tissue and, more particularly, to a surgical stapling apparatus for simultaneously applying biocompatible surgical fabric and a plurality of lines of staples to body tissue.

2. Description of the Related Art

In some surgical operations, surgical supports, e.g., meshes, are employed by surgeons to bridge, repair and/or reinforce tissue defects within a patient, especially those occurring in the abdominal wall, chest wall, diaphragm and other musculo-aponeurotic areas of the body. Surgical supports are disclosed in, e.g., U.S. Pat. Nos. 3,054,406, 3,124,136, 4,347,847, 4,655,221, 6,838,884 and 5,002,551. During such operations, surgeons employ conventional or known suturing or anchoring techniques to apply such supports to body tissue. For example, U.S. Pat. Nos. 4,652,245 and 5,203,864 describe methods for suturing or anchoring mesh supports to body tissue, especially during hernia repair operations.

Surgical stapling devices are employed by surgeons to sequentially or simultaneously apply one or more rows of surgical fasteners, e.g., staples or two-part fasteners, to body tissue for the purpose of joining segments of body tissue together. Such devices generally consist of a pair of jaws or finger-like structures between which body tissue to be joined is placed. When the instrument is actuated, or "fired," longitudinally moving firing bars contact staple drive members in one of the jaws, thereby pushing surgical staples through the body tissue and into an anvil in the opposite jaw which crimps the staples closed. If tissue is to be removed, a knife blade can be provided to cut between lines of staples. Examples of such instruments are described in U.S. Pat. Nos. 4,354,628, 5,014,899 and 5,040,715, each of which are incorporated herein by reference.

Surgical stapling devices have found widespread application in surgical operations where body tissue must be joined or removed. When operating on thin tissue, such as thin emphysematous lung tissue, it is important to effectively seal the tissue which can be particularly prone to air leakage. Preventing or reducing air leakage can significantly decrease post operative recovery time. Thus, it would be advantageous to provide structure for use with surgical stapling devices which enhances sealing at the surgical site.

SUMMARY OF THE INVENTION

These and other objects and advantages are accomplished herein by providing a surgical stapling apparatus wherein biocompatible surgical fabric is positioned adjacent or attached to a portion of the apparatus so that, upon actuation of the apparatus, both the fabric and a plurality of surgical fasteners are applied to body tissue. The fabric may serve as a bolster or support for the stapled union of tissue and/or impart a hemostatic or other therapeutic effect on the tissue. Briefly stated, the surgical stapling apparatus herein comprises a first jaw structure configured and dimensioned for housing a plurality of surgical fasteners, a second jaw structure disposed in juxtaposed alignment with the first jaw structure for effecting closure of a plurality of surgical fasteners and at least one biocompatible surgical fabric operatively associated with and releasably attached to either or both of the first and second jaw structures, wherein at least a portion of the fabric being disposed between the first and second jaw structures.

As more fully disclosed hereinafter, the biocompatible surgical fabric can be operatively associated with the first jaw structure, i.e., the cartridge frame, and/or the second jaw structure, i.e., the anvil frame, of a surgical stapling apparatus. The fabric can be woven, knit or nonwoven and be manufactured from bioabsorbable or nonbioabsorbable materials.

The term "biocompatible" as applied to the surgical fabric employed in this invention shall be understood to refer to the nontoxic and nonirritating nature of the fabric when maintained in contact with body tissue.

BRIEF DESCRIPTION OF THE DRAWINGS

Preferred embodiments of the invention are described hereinbelow, wherein.

DETAILED DESCRIPTION OF THE PREFERRED EMBODIMENTS

Figure 6:
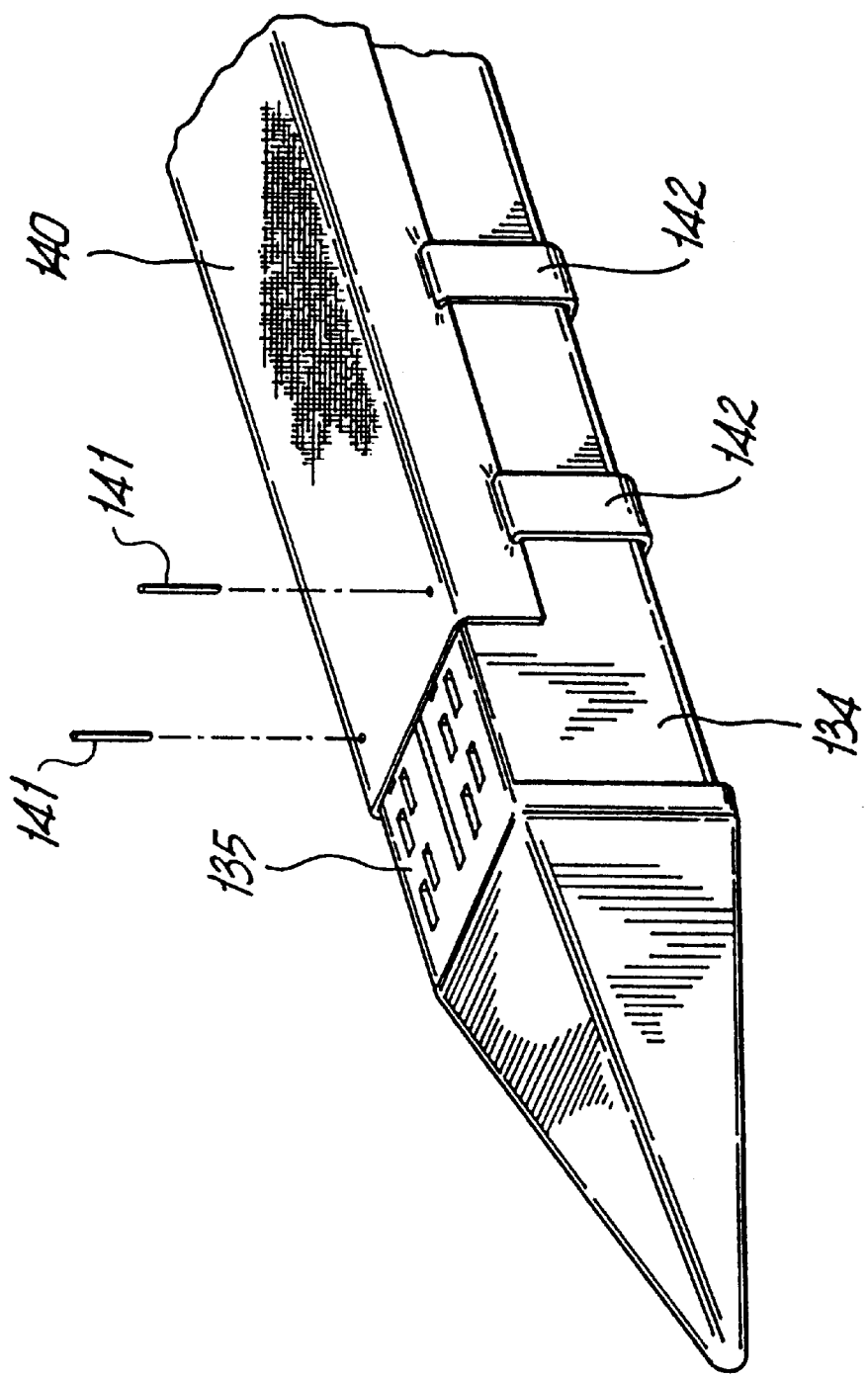
FIG. 6 is an enlarged perspective view depicting a distal portion of the cartridge assembly of a surgical stapling apparatus having the biocompatible surgical fabric depicted in FIG. 2 attached thereto by a plurality of clips.
Figure 7:
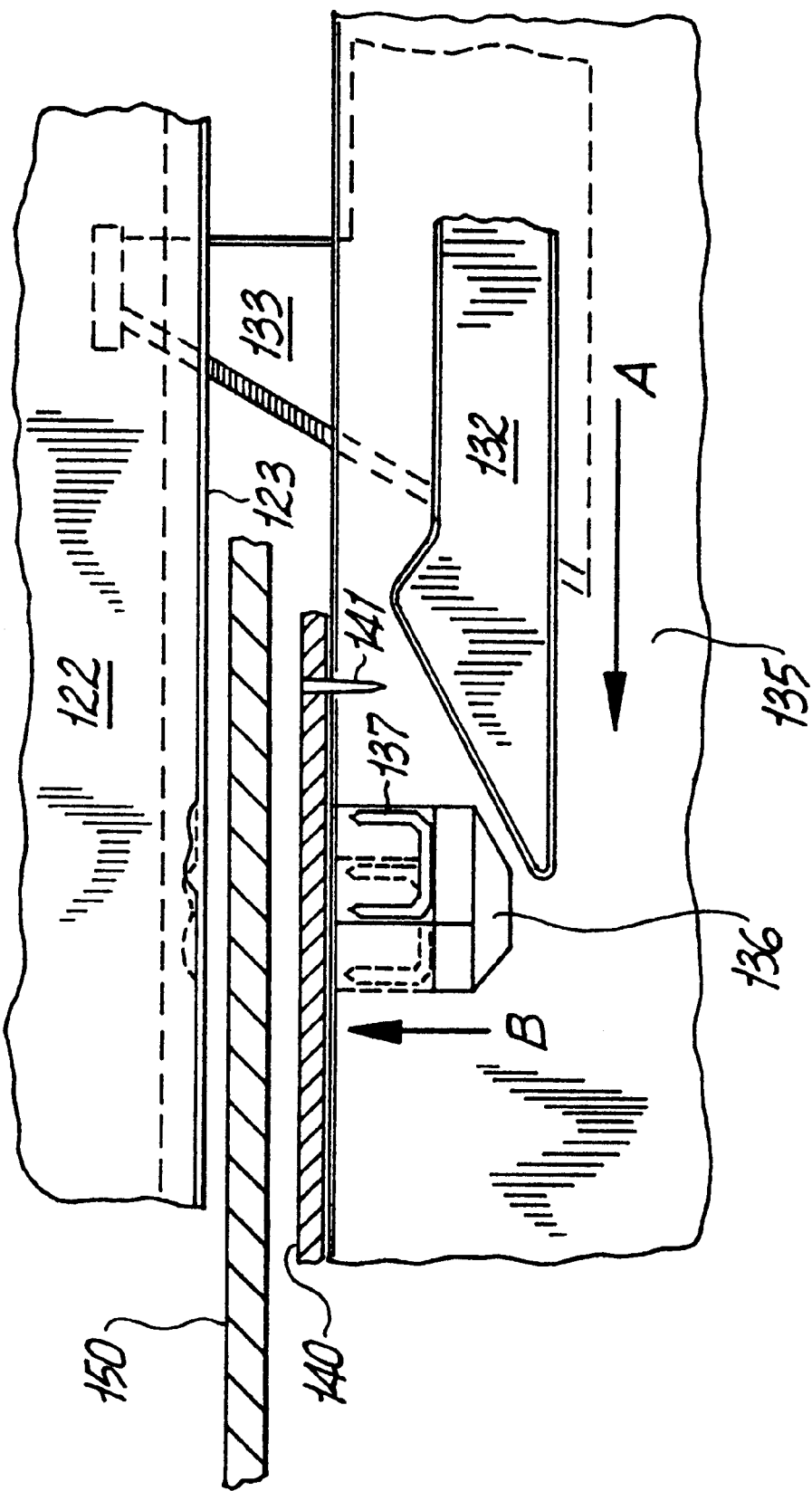
FIG. 7 is an enlarged cut-away side-view of the surgical stapling apparatus of FIG. 1 showing body tissue present between the biocompatible surgical fabric and the anvil portion of the apparatus.
Figure 8:
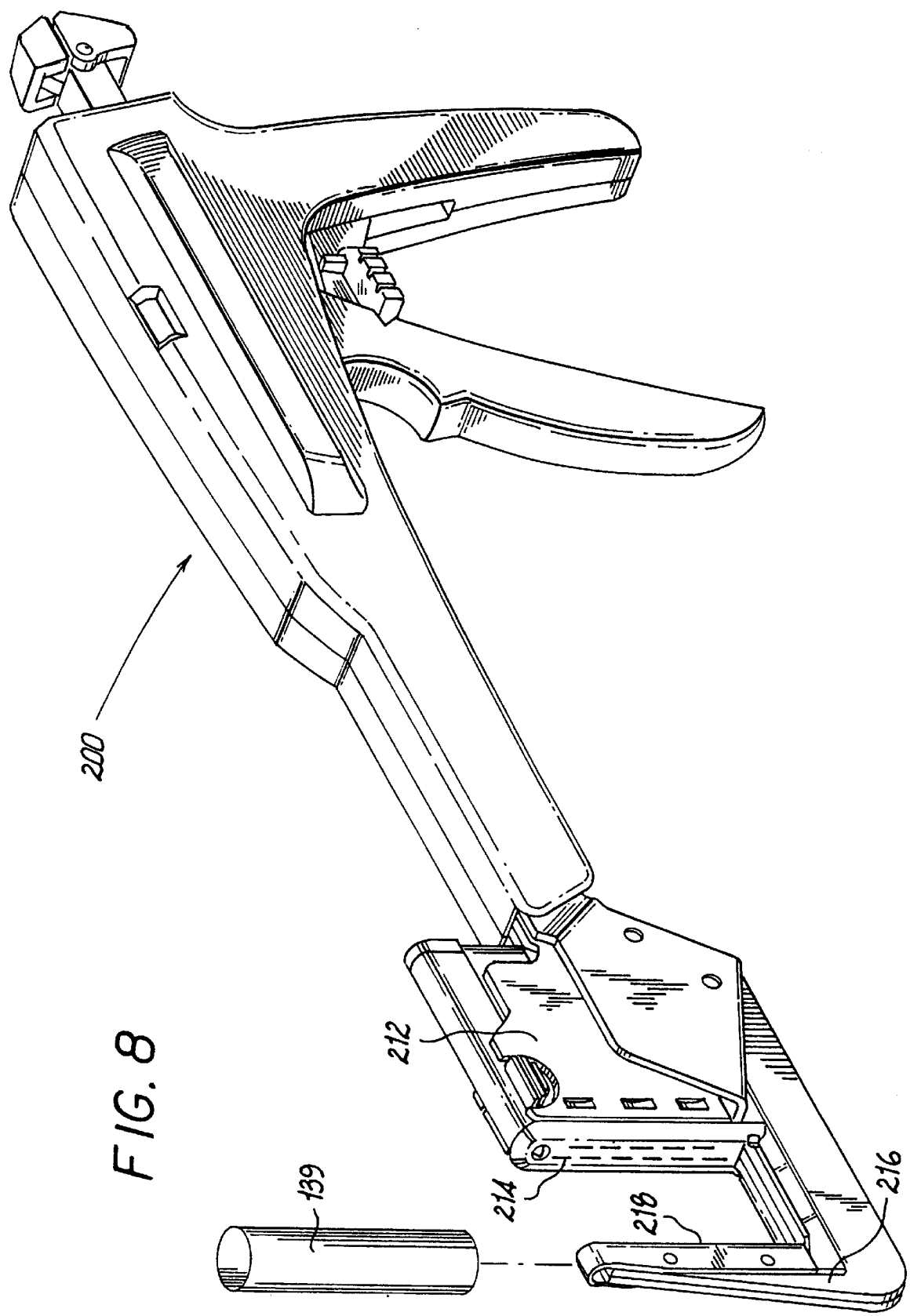
FIG. 8 is a perspective view of a surgical stapling apparatus having a biocompatible surgical fabric which is shaped in a tubular configuration.
Figure 9:
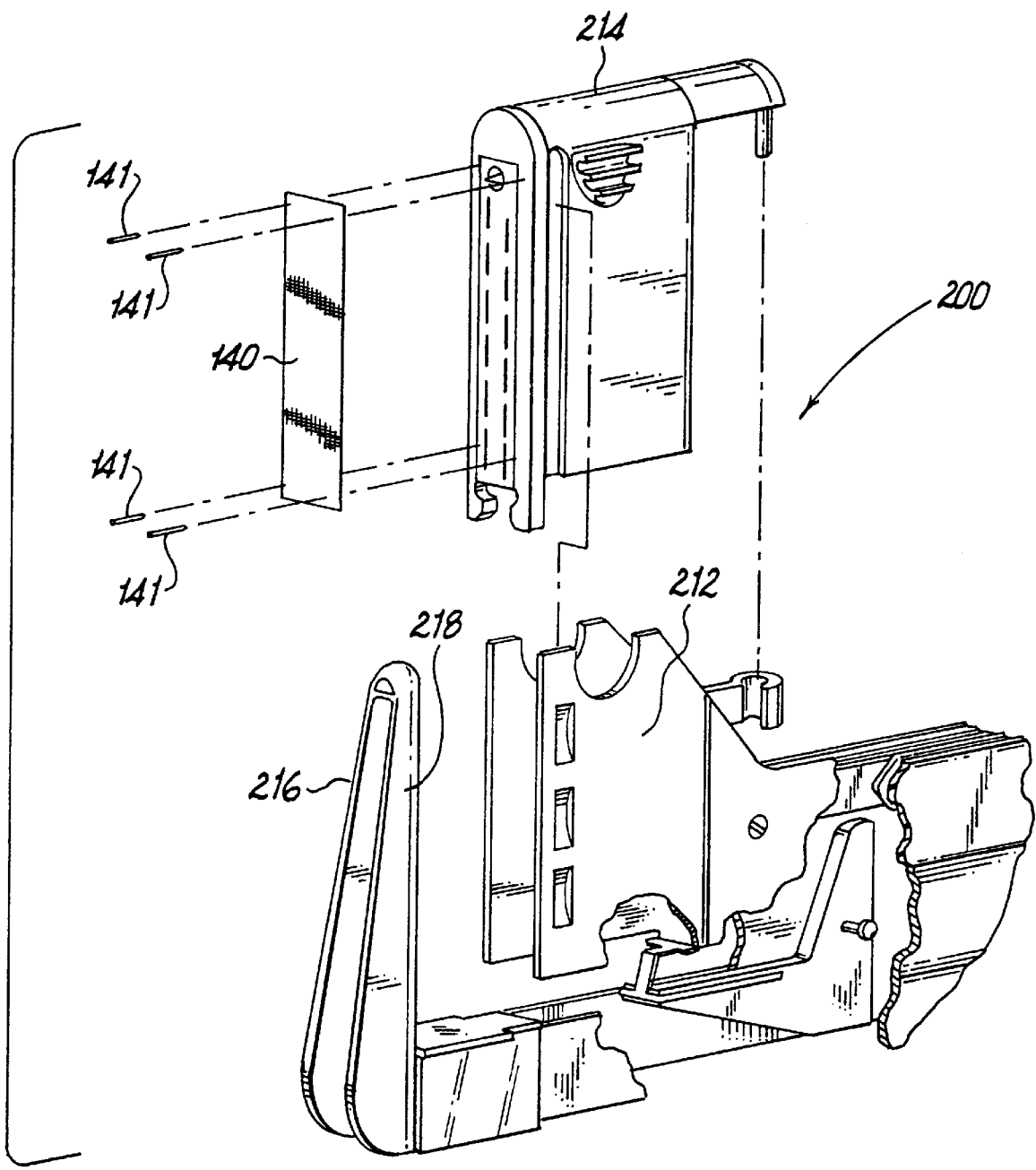
FIG. 9 is a partially cut away exploded perspective view depicting the separated parts of the distal end of the surgical stapling apparatus of FIG. 8.

The surgical stapling apparatus described herein includes a first jaw structure configured and dimensioned for housing a plurality of surgical fasteners, a second jaw structure configured and dimensioned for effecting closure of a plurality of fasteners and at least one biocompatible surgical fabric operatively associated with either of the first and second jaw structures, wherein at least a portion of the fabric is disposed between the first and second jaw structures. The specific design or type of surgical stapling apparatus employed in carrying out this invention is not critical so long as the basic structural elements are present. Thus, e.g., the apparatus can be one that is particularly suited for open surgery or, alternatively, for laparoscopic and/or endoscopic surgery. U.S. Pat. Nos. 5,014,899 and 5,040,715 disclose examples of sequentially firing stapling apparatus for open surgery and endoscopic surgery, respectively. Similarly, the apparatus can be one that applies surgical fasteners simultaneously, as in the case of U.S. Pat. No. 4,354,628. Substantially the same type apparatus as that disclosed and claimed in U.S. Pat. No. 5,014,899, supra, is depicted in FIGS. 1–7. Likewise, substantially the same apparatus disclosed and claimed in U.S. Pat. No. 4,354,678, supra, is depicted in FIGS. 8 and 9. While the embodiments of FIGS. 1–9 herein are preferred, the invention is equally applicable to other surgical stapling apparatus such as that disclosed and claimed in U.S. Pat. No. 5,040,715, supra.

Referring to FIGS. 1–3 and 5, surgical stapling apparatus shown generally at 100 comprises a first jaw structure 110 having a finger-like projection 111 for holding actuating assembly 130. A second jaw structure 120 includes a pair of hinge plates 121 for hingedly connecting to first jaw structure 110 and a finger-like projection 122 for carrying an anvil assembly 123. Anvil assembly 123 is formed of a plate with indentations or depressions which deform the legs of metal staples housed in cartridge assembly 135 of actuating assembly 130. Alternatively, the anvil assembly can include means for holding rows of the retainer portions of two-part surgical fasteners as more fully described in U.S. Pat. No. 5,156,315, the contents of which are hereby incorporated by reference herein.

Disposable loading unit 130 of this embodiment of the present invention is a replaceable unit which includes a pusher assembly having a thrust knob 131, cam bars 132 and, optionally, knife blade 133. Disposable loading unit 130 further includes stationary carrier 134 for holding cartridge assembly 135.

Referring now to FIGS. 8 and 9, surgical stapling apparatus 200 comprises a first jaw structure 212 for holding cartridge assembly 214. Cartridge assembly 214 carries a plurality of rows of staples which, upon actuation of the apparatus, substantially simultaneously strike anvil assembly 218 on second jaw member 216 to effect closure. Anvil assembly 218 is formed of a plate with indentations or depressions which deform the legs of metal staples housed in cartridge assembly 214.

Figure 1:
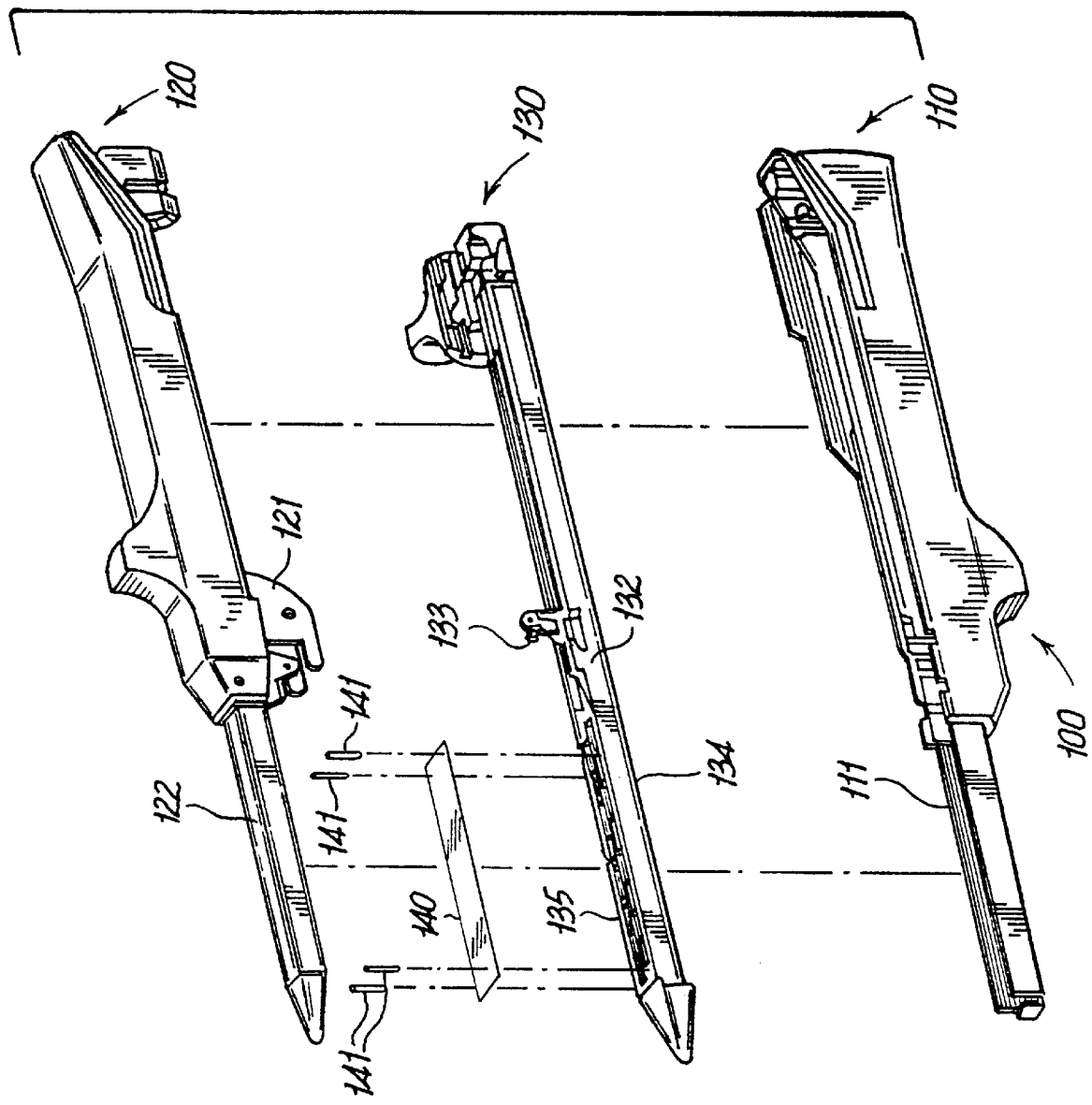
FIG. 1 is a perspective view depicting the separated parts of a surgical stapling apparatus having attached thereto a biocompatible surgical fabric which is dimensioned to substantially conform to the tissue contacting surface dimensions of the cartridge assembly.
Figure 2:
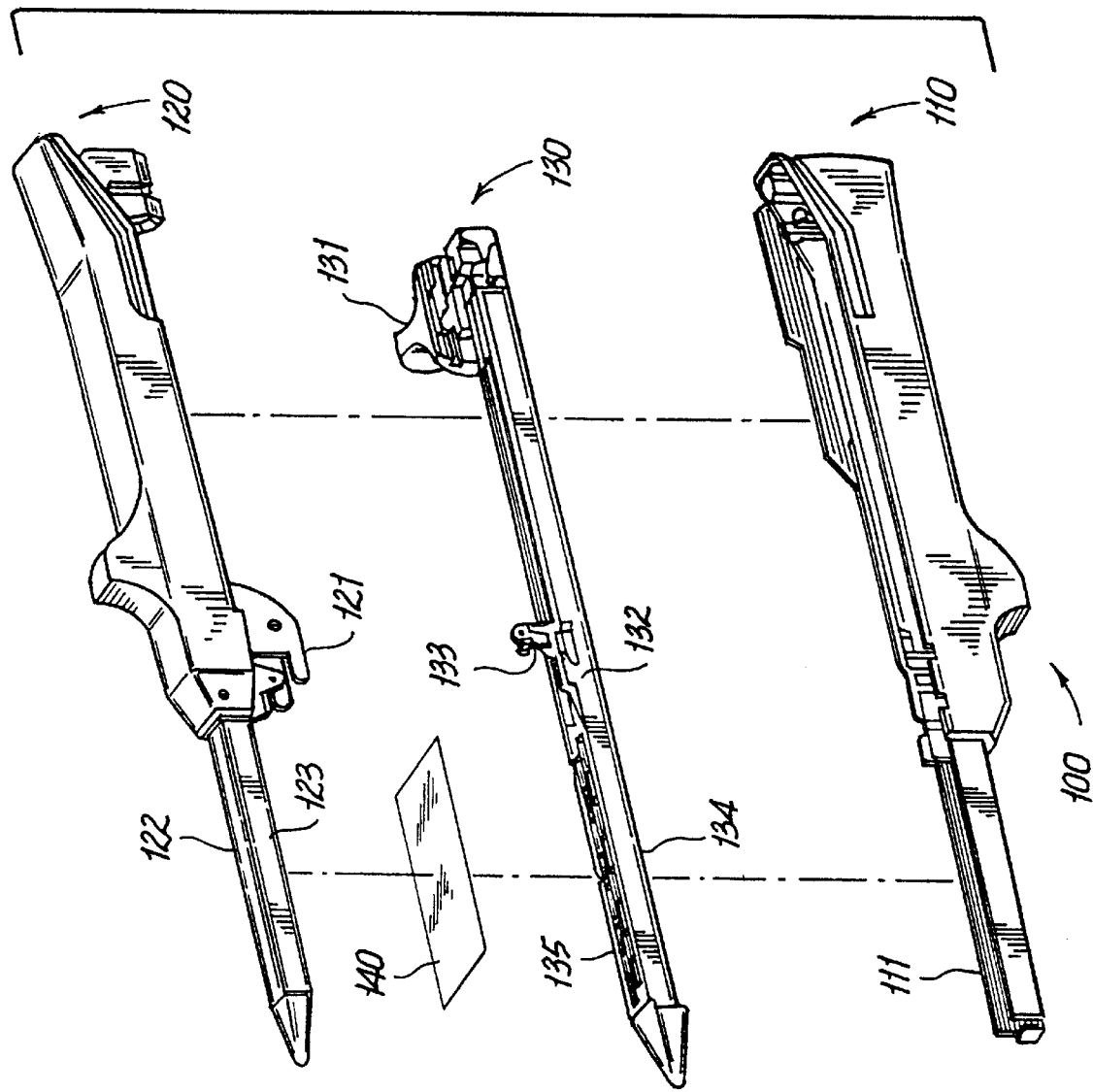
FIG. 2 is a perspective view depicting the separated parts of a surgical stapling apparatus having attached thereto a biocompatible surgical fabric which is configured larger than the tissue contacting surface dimensions of the cartridge assembly.
Figure 3:
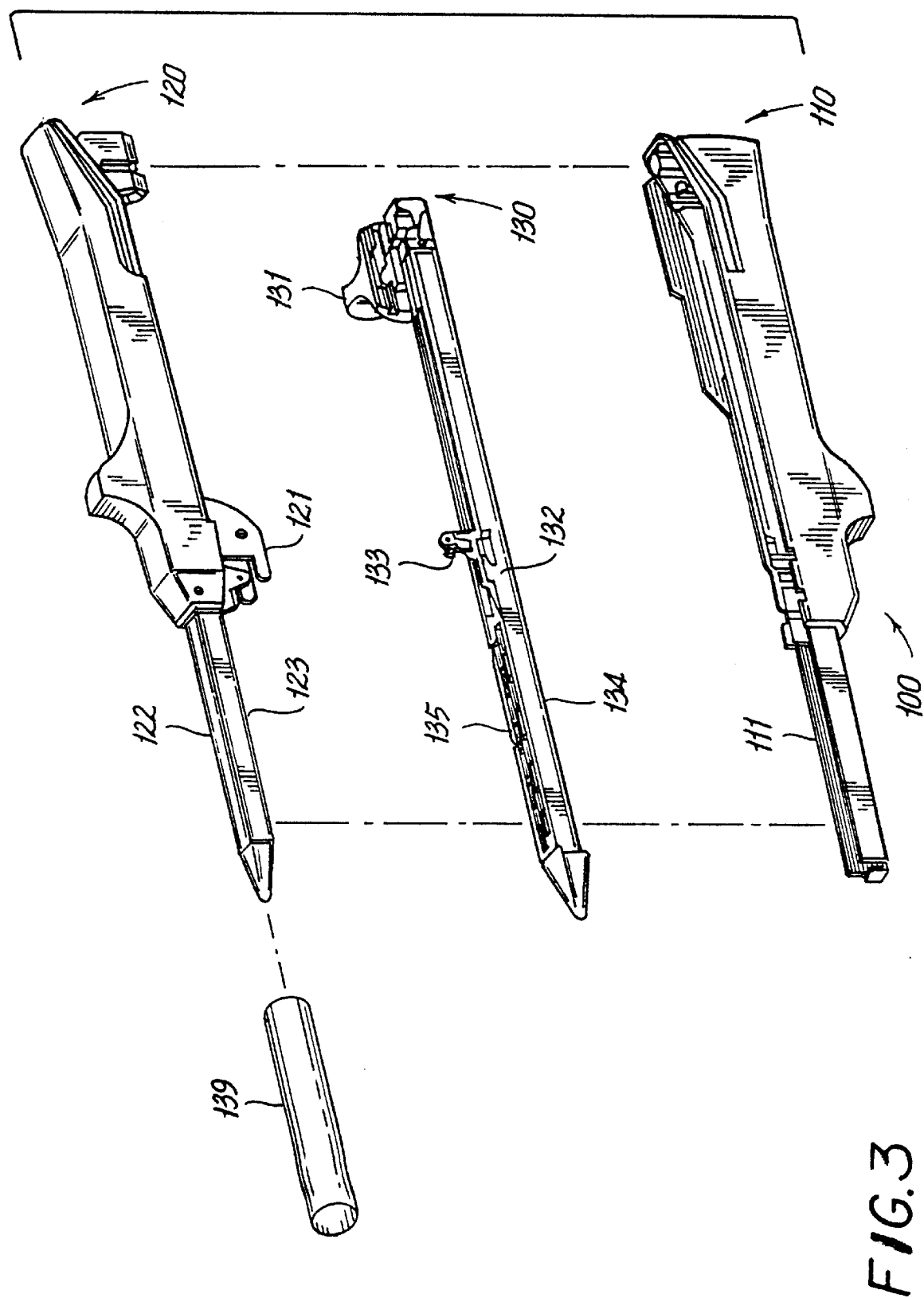
FIG. 3 is a perspective view depicting the separated parts of a surgical stapling apparatus having associated therewith a biocompatible surgical fabric which is shaped in a tubular configuration.
Figure 4:
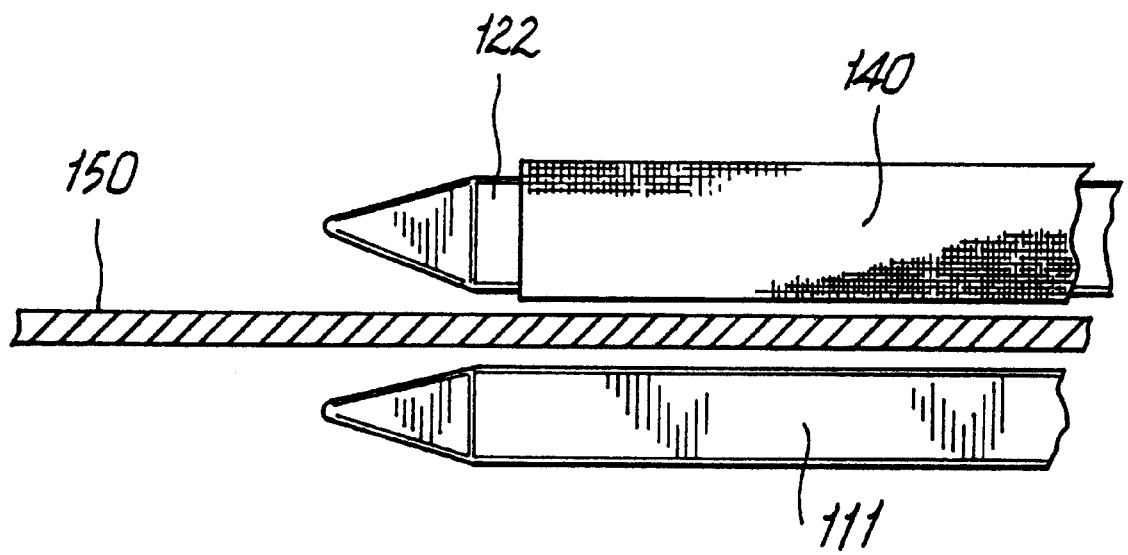
FIG. 4 is an enlarged side-view of the distal end of one embodiment of the surgical stapling apparatus of the present invention engaging body tissue.

Biocompatible surgical fabric 139, 140 is partially or completely disposed between anvil assembly 123 and cartridge assembly 135 as shown, e.g., in FIGS. 1–5, or anvil assembly 218 and cartridge assembly 214, as shown in FIGS. 8 and 9. Fabric 139, 140 can be shaped to any desired configuration. Thus, e.g., in FIGS. 1, 2, 4–7 and 9 fabric 140 is planar while in FIGS. 3, 5 and 8 fabric 139 is tubular. When planar, fabric 140 can be shaped to correspond substantially in size with the tissue contacting surface dimensions of either anvil assembly 123 or cartridge assembly 135 as depicted in FIG. 1 or be wider as depicted in FIGS. 2 and 6.

Figure 5:
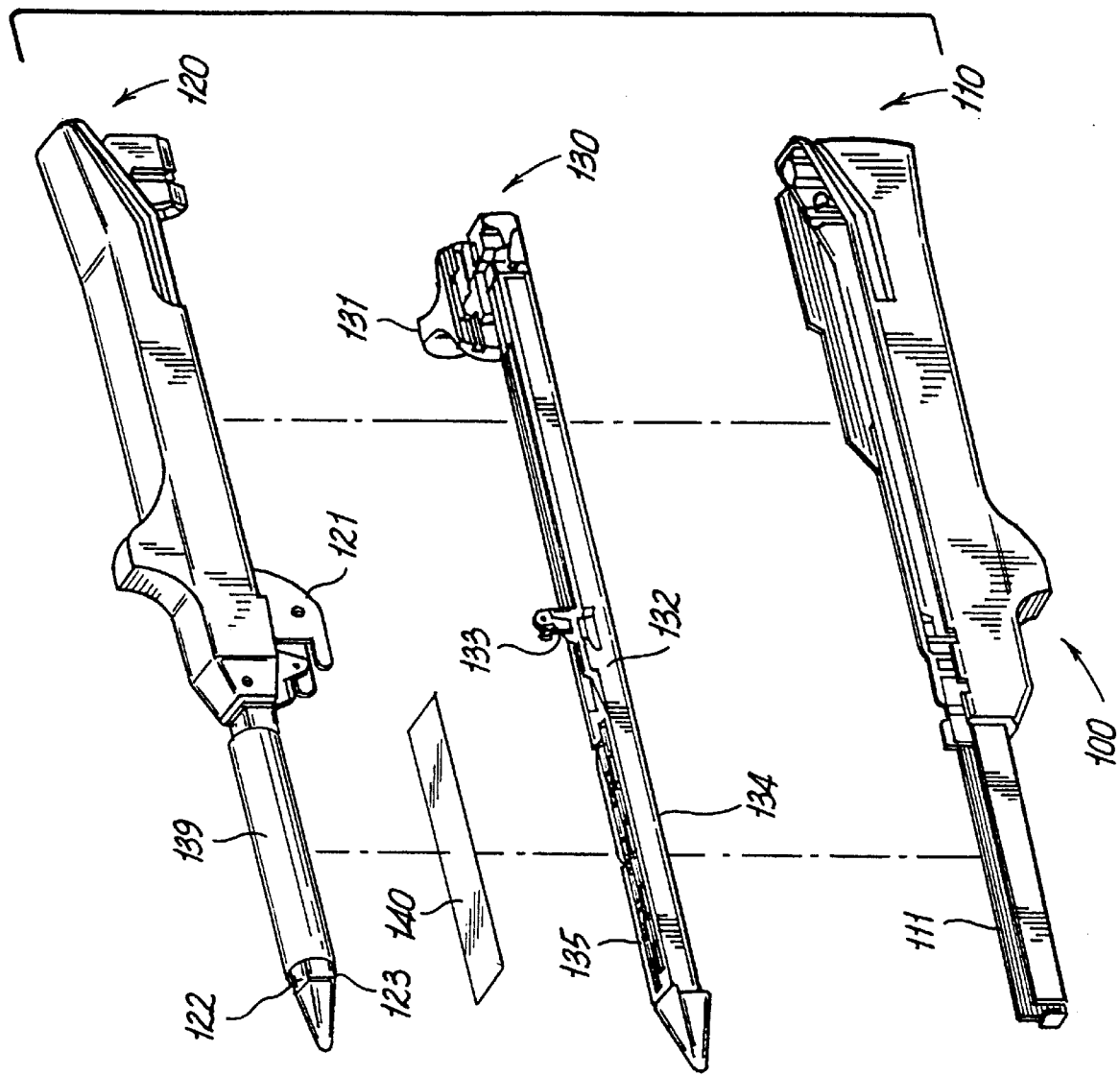
FIG. 5 is a perspective view depicting the separated parts of a surgical stapling apparatus having associated therewith a tubular shaped biocompatible surgical fabric positioned over the anvil assembly and a planar fabric positioned over the cartridge assembly of the apparatus.

As shown in FIG. 5, one or more individual pieces or segments of biocompatible surgical fabric can be employed in carrying out the present invention. Therefore, it is contemplated that two or more pieces or layers of fabric can be attached to a surgical stapling device as herein disclosed. For example, tubular fabric prosthesis 139 is fitted over anvil portion 122 and a planar fabric prosthesis 140 is attached to cartridge assembly 135 of stapling apparatus 100. In such a case, body tissue is sandwiched between and secured to both prostheses 139, 140, thereby providing fabric at both the entry and exit points of the staples or fasteners. The tubular prosthesis can be subsequently cut longitudinally along its longest axis to provide free ends which can be stapled or otherwise affixed to surrounding tissue and/or organs for further structural support.

Biocompatible surgical fabric 139, 140 can be woven, knit or nonwoven and can be bioabsorbable or nonbioabsorbable. Nonwoven bioabsorbable fabric is generally preferred in carrying out this invention. Bioabsorbable surgical fabrics include those fabricated from homopolymers, copolymers or blends obtained from one or more monomers selected from the group consisting of glycolide, glycolic acid, lactide, lactic acid, p-dioxanone, α-caprolactone and trimethylene carbonate. Bioabsorbable surgical fabrics, especially those that are nonwoven, manufactured from copolymers of glycolide and lactide are preferred. U.S. Pat. Nos. 3,875,937, 3,937,223 and 4,128,612 describe bioabsorbable surgical fabrics suitable for use with the present invention. Nonbioabsorbable surgical fabrics include those that are fabricated from such polymers as polyethylene, polypropylene, nylon, polyethylene terephthalate, polytetrafluoroethylene, polyvinylidene fluoride, and the like.

Fabric 139, 140 is releasably attached to either anvil assembly 123 or cartridge assembly 135 as shown in FIGS. 1–4 or either anvil assembly 218 or cartridge assembly 214 as shown in FIGS. 8 and 9. Alternatively, the anvil assembly and cartridge assembly can both have fabric disposed thereon (FIG. 5), in any combination of tubular and planar structure, to provide a tissue/fabric "sandwich" upon actuation of the instrument.

The attachment of the fabric to a surgical stapling device in accordance with this invention should be secure enough to prevent the fabric from slipping off the device, yet not be so strong as to inhibit separation of the fabric from the device after the device has been actuated. Such releasable attachment can advantageously be effected by employing a plurality of pins 141 as illustrated in FIGS. 1, 7 and 9. As shown in FIG. 6, clips 142 may also be employed as the securing means. A combination of pins and/or clips can also be employed. The precise number and location of pins and/or clips is not critical so long as the surgical fabric is releasably attached to the stapling apparatus.

Operation of a surgical stapling apparatus falling within the scope of this invention is illustrated in FIG. 7. Cartridge assembly 135 includes pusher members 136 which are acted upon by slidably mounted cam bar 132. Upon movement of cam bar 132 in the direction indicated as "A", pusher members 136 exert an upwardly-directed force B on staples 137 housed in cartridge assembly 135. Staples 137 penetrate fabric 140 (secured to cartridge assembly 135 by a plurality of pins 141) and tissue layer 150. Thereafter, staples 137 strike anvil assembly 123 for closure. Following actuation, the stapling apparatus is withdrawn from the stapling site, thus leaving behind a fabric prosthesis stapled to body tissue with a plurality of rows of staples.

Fabric prosthesis 160 can act as an adhesion barrier, hemostatic agent, reinforcement, tissue growth enhancer, and the like. Furthermore, it shall be understood that fabric prosthesis 140 can have incorporated therein and/or thereon one or more medically and/or surgically useful substances such as drugs, enzymes, growth factors, peptides, proteins, dyes, diagnostic agents or hemostasis agents.

While this invention has been disclosed herein in connection with certain embodiments and certain structural and procedural details, it is clear that changes, modifications or equivalents can be used by those skilled in the art. For example, when a knife blade is used in conjunction with a surgical stapler, the fabric can be pre-cut or weakened to facilitate passage of the blade between or through the fabric. Accordingly, such changes within the principles of this invention are intended to be included within the scope of the claims below.

What is claimed is:

1. A surgical stapler having in combination an anvil portion and a generally tubular tissue bolstering member fabricated from polytetrafluoroethylene, the tissue bolstering member being fitted around the stapler anvil portion.

2. The combination of claim 1, wherein the tissue bolstering member is elongated and has first and second openings for receiving the stapler anvil portion.

3. The combination of claim 1, wherein a portion of the tissue bolstering member is weakened.

4. A method of applying surgical bolstering material to body tissue comprising:
    providing a surgical stapler having first and second jaw structures;
    providing a first, generally tubular surgical bolstering member fabricated from polytetrafluoroethylene;
    disposing the first tissue bolstering member over one of the stapler jaw structures;
    positioning the jaw structures of the stapler on either side of tissue to be stapled; and
    firing the stapler to drive staples through the bolstering member and tissue.

5. A method of applying surgical bolstering material to body tissue comprising;
    providing a surgical stapler having an anvil jaw and a staple cartridge jaw;
    selecting a first, generally tubular bolstering member fabricated from polytetrafluoroethylene;
    fitting the first bolstering member over the staple cartridge jaw of the stapler, such that the bolstering member generally surrounds the staple cartridge jaw;
    selecting a second bolstering member fabricated from polytetrafluoroethylene;
    fitting the second bolstering member over the staple cartridge jaw of the stapler, such that the bolstering member generally surrounds the staple cartridge jaw;
    positioning the stapler jaws having the bolstering members fitted thereon on either side of tissue to be stapled; and
    firing the stapler to drive staples through the bolstering members and tissue.

6. The combination of claim 2, wherein a portion of the tissue bolstering member is weakened.

7. The method of claim 4, further comprising the step of weakening at least a portion of the bolstering member.

8. The method of claim 5, further comprising the step of weakening at least a portion of the first and second bolstering members.

9. A surgical stapler having in combination an anvil portion and a generally tubular tissue bolstering member fabricated from polytetrafluoroethylene, the tissue bolstering member being fitted around the stapler anvil portion and having first and second openings for receiving the stapler anvil portion.

10. A surgical stapler having in combination an anvil portion, a stapling containing portion, and a tissue bolstering member being fitted around the outer surface of at least the anvil portion, the tissue bolstering member defining a continuous sheet of material having an interior surface and an exterior surface, the interior surface of the tissue bolstering material facing the outer surface of the anvil portion when the tissue bolstering material is fitted around the anvil portion.

11. The surgical stapler of claim 10, wherein the sheet is seamless.

12. The surgical stapler of claim 10, wherein the sheet is fabricated from polytetrafluoroethylene.

13. A surgical apparatus for driving surgical fasteners into body tissue comprising:
    a first jaw structure for housing a plurality of surgical fasteners and having an outer perimetal surface;
    a second jaw structure being disposed in juxtaposed alignment with the first jaw structure to effect closure of said plurality of fasteners and having an outer perimetal surface; and
    a continuous wrap of biocompatible surgical fabric disposed around the outer perimetal surface of at least one of the first and second jaw structures, the wrap having an interior surface and an exterior surface, such that the interior surface of the wrap faces an outer perimetal surface of the first or second jaw structure when the wrap is disposed around the jaw structure.

14. A surgical apparatus according to claim 13, wherein the wrap is seamless.

15. A surgical apparatus according to claim 13, wherein the wrap is fabricated from polytetrafluoroethylene.

\* \* \* \* \*